United States Patent [19]

Litzaw

[11] Patent Number: 4,907,613
[45] Date of Patent: Mar. 13, 1990

[54] CONTACT LENS CLEANING DEVICE

[76] Inventor: Edgar M. Litzaw, 50 Tiburon St., Bay 14, San Rafael, Calif. 94901

[21] Appl. No.: 243,471

[22] Filed: Sep. 12, 1988

[51] Int. Cl.$^4$ ............................................... B08B 3/04
[52] U.S. Cl. ................................... 134/158; 134/184;
    134/161; 134/164; 134/196; 74/25
[58] Field of Search ............... 134/184, 161, 196, 197,
    134/158, 164; 68/170; 74/25, 42, 47

[56] References Cited
U.S. PATENT DOCUMENTS

| | | | |
|---|---|---|---|
| 1,825,584 | 9/1931 | Donley | 68/170 X |
| 3,139,097 | 6/1964 | Hungerford et al. | 134/197 X |
| 3,139,098 | 6/1964 | Hungerford et al. | 134/197 X |
| 3,825,019 | 7/1974 | Hall | 134/196 X |
| 4,653,519 | 3/1987 | Kanner | 134/161 |
| 4,779,633 | 10/1988 | Thomas et al. | 134/196 |

Primary Examiner—Frankie L. Stinson
Attorney, Agent, or Firm—Larry D. Johnson

[57] ABSTRACT

A contact lens cleaning device provides a mechanical apparatus for the thorough agitation and cleaning of contact lenses immersed in a disinfecting solution. The device comprises a base portion bearing a reservoir for containing a measured amount of disinfecting solution, and a main housing portion including a lens holder portion for releasable capture of the contact lenses to be cleaned. The lens holder is connected to rotating crankshafts by connecting rods, and the crankshafts are connected to a knob on the outside of the main housing, so that rotary motion of the crankshafts is translated to reciprocating motion of the lens holder.

4 Claims, 8 Drawing Sheets

CONTACT LENS CLEANING DEVICE

BACKGROUND OF THE INVENTION

1. Field of the Invention

This invention relates generally to optically corrective contact lenses and related accessories therefor, and more specifically to an improved apparatus for the cleaning and disinfecting of contact lenses.

2. Description of the Prior Art

Optically corrective contact lenses are an extremely popular aid for improving vision. Typically, such lenses must be regularly removed from the user's eye and thoroughly cleaned and disinfected, to prevent bacterial infection in the eye. Most common contact lens cleaning regimens include immersion of the lenses into a cleaning and/or disinfecting solution for a prescribed period of time. It has been determined that mere static immersion of the lenses in these solutions may not be sufficient for the desired degree of disinfection. Accordingly, several mechanical devices have been developed to additionally agitate the lenses while in the solution, in an effort to enhance the disinfection action. One type of mechanical device merely vibrates the vessel containing the lenses and solution. Unfortunately, such vibratory units yield little benefit in cleaning and disinfecting ability. Other devices have been developed which require placement of the lenses in a carrier, and rotation of the carrier about a central axis within the disinfecting solution. However, this arrangement offers little cleaning action of the lenses near the center of the axis. Still other cleaning devices attempt to clean the lenses by attachment of such a carrier to a plunger-type structure, requiring manual reciprocation of the plunger within the solution. These devices tend to be awkward and difficult to use, thereby defeating their purpose.

SUMMARY OF THE INVENTION

The contact lens cleaning device of this invention provides an efficient mechanical apparatus for the thorough agitation and cleaning of contact lenses in a disinfecting solution. The device comprises a base portion bearing an internal cavity or reservoir for containing a measured amount of disinfecting solution, and a main housing portion including a lens holder portion for releasable capture of the contact lenses to be cleaned. The lens holder is connected to one or more rotating crankshafts by one or more connecting rods, and the crankshaft is connected to a knob on the outside of the main housing, so that rotary motion of the crankshaft is translated to reciprocating motion of the lens holder. Thus, when the main housing is attached to the base portion, and the lens holder is immersed in the disinfecting solution, manual rotation of the knob causes the lens holder to reciprocatingly agitate the lenses within the solution.

In the preferred embodiment, the main housing includes a pair of crankshafts each driven by a single internal ring gear and rotating in the same direction. These crankshafts each terminate in an off-center crankpin, which is then connected to a mating pivot hole in a pair of lens holder connecting rods. These connecting rods diverge to their hinge connection at the ends of the lens holder. This geometrical arrangement (spacing of the lens holder hinges greater than the center-to-center spacing of the crankpins) results in a desirable "rocking" motion in addition to the normal up-and-down reciprocation of the lens holder. Thus, the lens holder is in a horizontal attitude only at the extreme top and bottom of travel, and through the rest of the stroke, the two sides of the lens holder change speed relative to one another.

In an alternate embodiment, counter-rotating crankshafts (e.g., through the use of an included idler gear) drive the connecting rods, resulting in a more-or-less "pure" reciprocating action for the lens holder. Of course, any other mechanical arrangement to convert the rotating motion to reciprocating motion could be used. For example, instead of the use of gears and crankshafts, a cam design using an oscillating channel in the knob to drive a rocker arm, or a pair of pivoted levers, could be used.

The advantage to any such reciprocating device is that the disinfecting solution is cause to flow through the lens holder and rapidly reversing directions. This provides superior cleaning ability and high efficiency in reducing the number of contaminates and bacteria.

The present invention provides other improvements for a lens cleaning device, particularly as applied to this reciprocating system. For example, the lens baskets of lens holders traditionally include an outer basket and inner lens support each consisting of radially-extending cross straps to capture the lens within the basket. Applicant's device specifically offsets these radial "webs", so that the lens is cause to flex in opposite directions while undergoing the reciprocating reversal directions.

In addition, the lens holder itself includes structural "dams" (obstacles) to fluid flow, forcing the disinfecting solution to flow through the lens baskets themselves. For example, the hinged tops of the connecting rods extend completely across the lens holder, forming a barrier to fluid flow past the ends of the holder. In addition, the lens holder may specifically include a central guide bar to stabilize possible side motion, and this guide bar similarly forms a barrier to fluid flow between the respective sides of the holder.

DETAILED DESCRIPTION OF A PREFERRED EMBODIMENT

Figure 1:
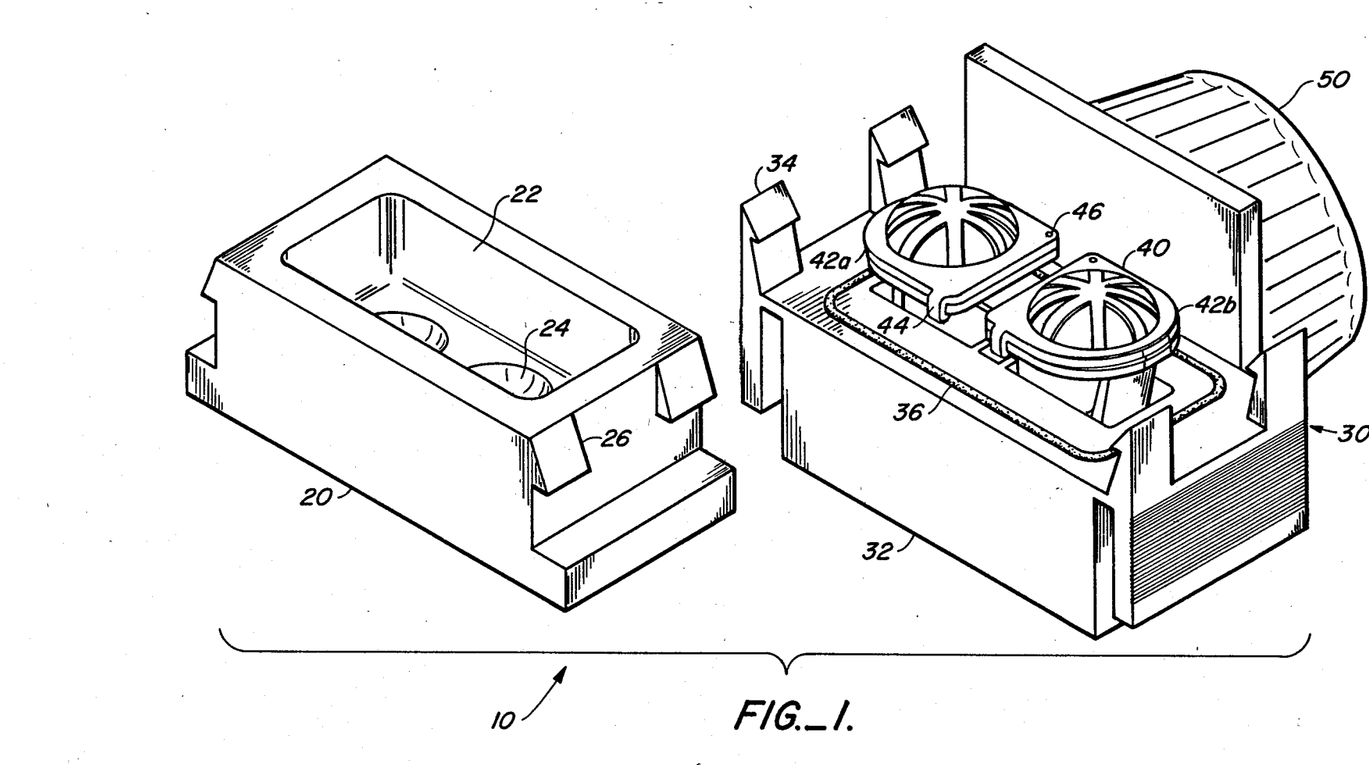
FIG. 1 is a perspective (pictorial) view of the contact lens cleaning device of this invention with its two main portions separated: the base portion in its normal position for filling with disinfecting solution, and the main housing portion in a position for loading or unloading of contact lenses into the lens holder.

FIG. 1 is a perspective (pictorial) view of a contact lens cleaning device 10 of this invention with its two main portions separated: a base portion 20 in its normal position for filling with disinfecting solution, and a main housing portion 30 in a position for loading or unloading of contact lenses. Base 20 includes an internal cavity or reservoir 22 into which a measured amount (typically eight milliliters) of cleaning/disinfecting solution is poured. Reservoir 22 includes a pair of depressions 24 that accommodate the maximum extension of the lens holder in its downward stroke, as described infra. Base 20 may also include a plurality of detents 26 which provide a mating surface for the attachment mechanism of the device.

Main housing 30 includes body 32 with clamp 34 for releasable engagement of base detent 26. Gasket 36 provides a more positive seal with base 20 when assembled. Carried within body 32 is lens holder 40 comprising a pair of lens baskets 42a, b, each bearing a latch 44 and alignment hole 46 for secure closure. Lens holder 40 is driven in reciprocating motion by rotation of knob 50, as described infra.

Figure 2:
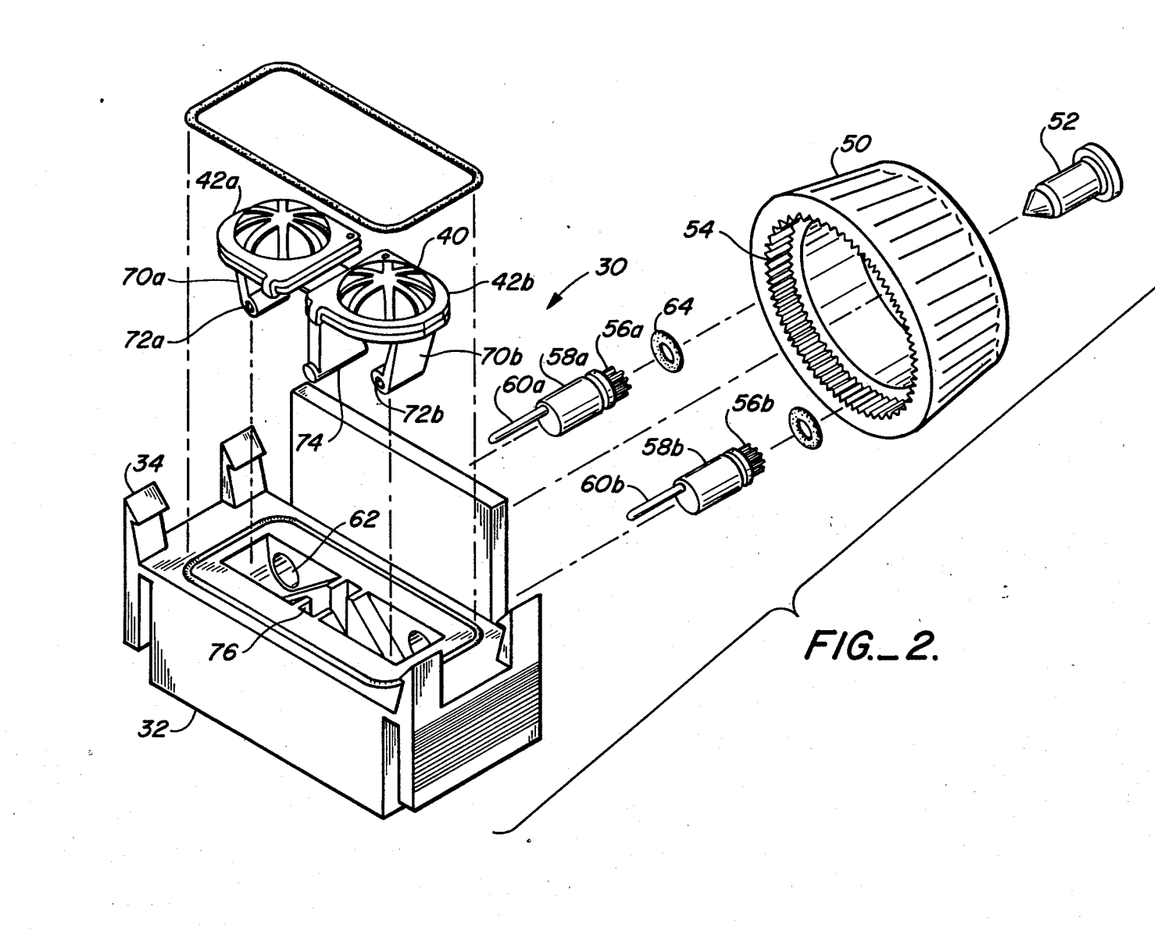
FIG. 2 is an exploded perspective view of the main housing portion of the contact lens cleaning device, illustrating the assembly relationship of its mechanical components.

FIG. 2 is an exploded perspective view of the main housing portion 30 of the contact lens cleaning device, illustrating the assembly relationship of its mechanical components. Knob 50 is attached to body 32 by pin 52. The knob incorporates an internal ring gear 54 which engages and drives a pair of pinions 56a, b on crankshafts 58a, b, respectively. These crankshafts terminate in offset (off-center) crankpins 60a, b. The crankshafts penetrate body 32 through crankshaft holes 62, and may be sealed by use of 0-rings 64.

When assembled, crankpins 60 engage connecting rods 70a, b at pivot holes 72a, b. These connecting rods attach to the remote ends of lens holder 40. Side motion stabilizer or guide bar 74 rides in guide bar slot 76 of body 32.

Figure 3:
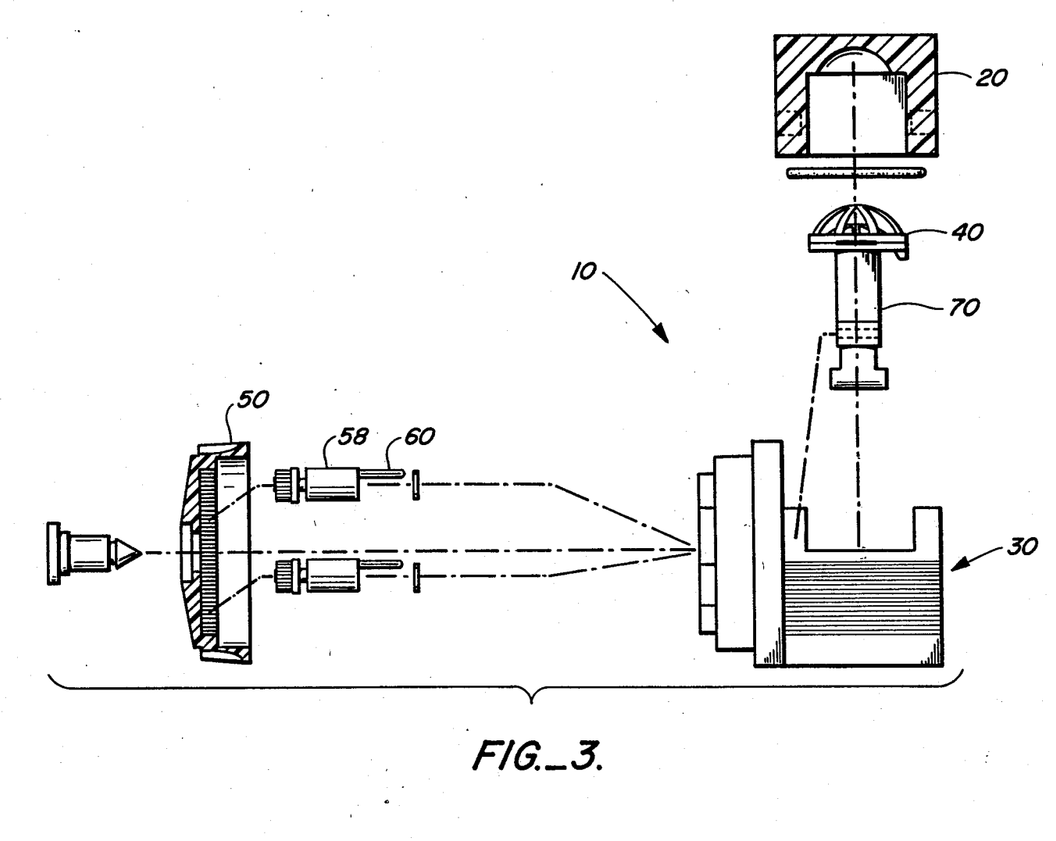
FIG. 3 is an exploded side view in partial section of the contact lens cleaning device, with the base portion shown inverted over the main housing portion for illustration only.

FIG. 3 is an exploded side view in partial section of the contact lens cleaning device 10, with the base portion 20 shown inverted over the main housing portion 30 for illustration only. This view further illustrates the assembly of knob 50, crankpins 60 (note: crankshafts 58a, b are actually side-by-side), connecting rod 70, and lens holder 40.

Figure 4:
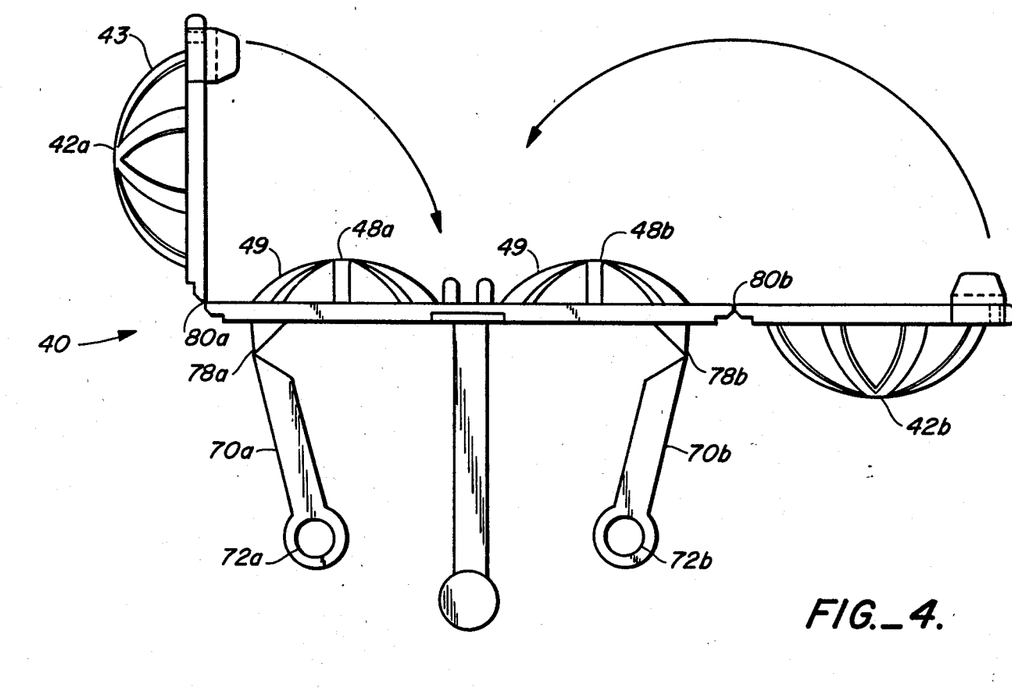
FIG. 4 is a front elevation schematic view of the lens holder portion of the main housing of the contact lens cleaning device illustrating the two lens baskets in different stages of opened position.

FIG. 4 is a front elevation schematic view of the lens holder portion 40 of the contact lens cleaning device. Connecting rods 70a, b attach to lens holder 40 at hinges 78a, b. Lens baskets 42a, b attach to holder 40 at hinges 80a, b. Baskets 42a, b comprise a radial web of cross straps 43, while inner lens supports 48a, b comprise a radial web of cross straps 49, which are preferably offset to cross straps 43.

Figure 5:
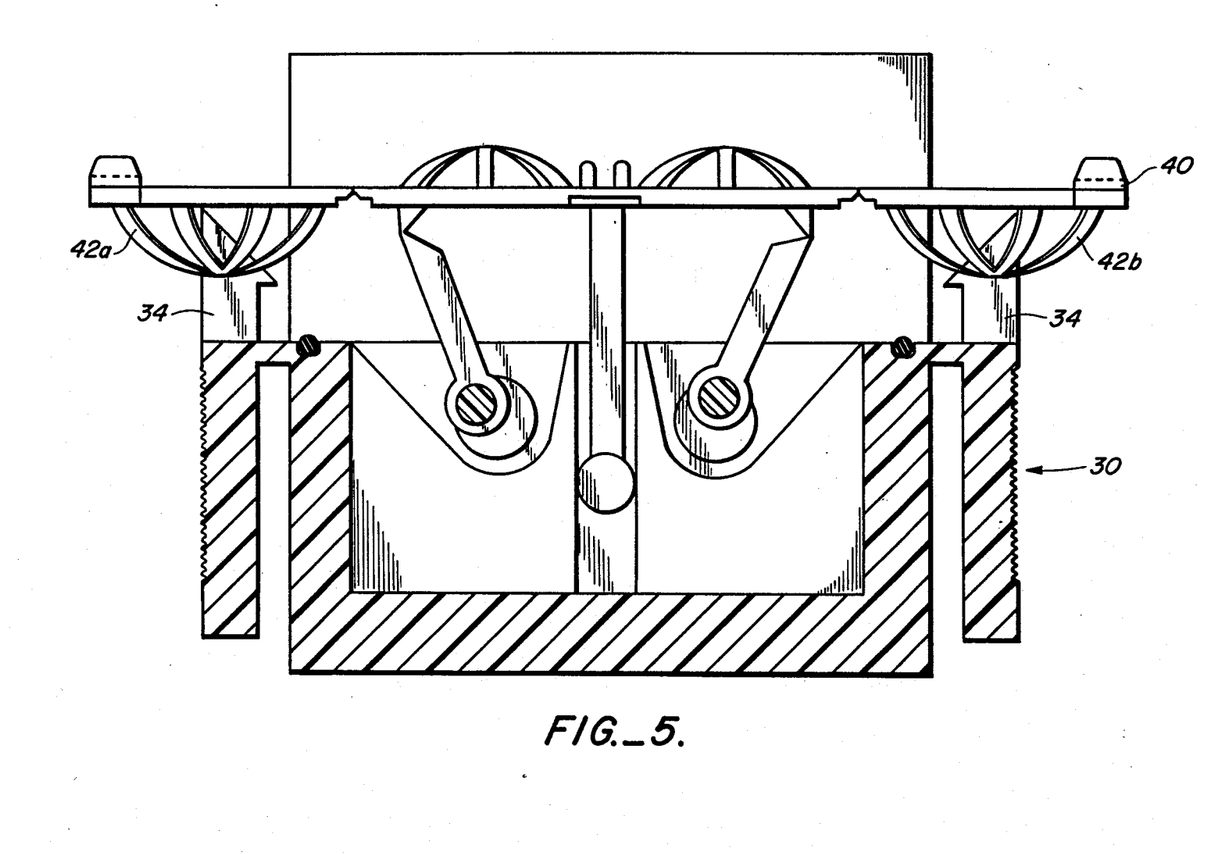
FIG. 5 is a partially cutaway front elevation schematic view of the main housing portion of the contact lens cleaning device illustrating both lens baskets of the lens holder in their completely open position for loading or unloading of contact lenses.

FIG. 5 is a partially cutaway front elevation schematic view of the main housing portion 30 of the contact lens cleaning device illustrating both lens baskets 42a, b of the lens holder 40 in their completely open position for loading or unloading of contact lenses. This view illustrates that the baskets 42a, b may be fully opened without interference by clamp 34.

Figure 6:
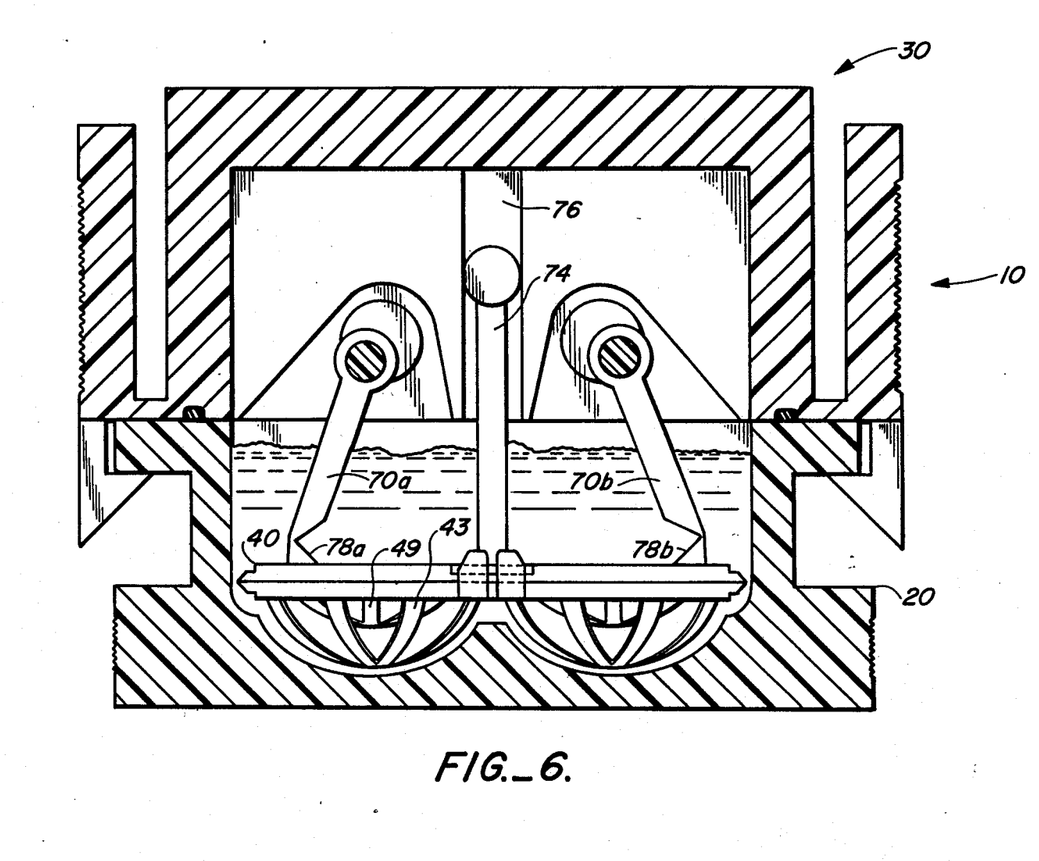
FIG. 6 is a partially cutaway side elevation schematic view of the contact lens cleaning device of this invention, illustrating normal operation with the main housing portion inverted over and attached to the solution-filled base portion.

FIG. 6 is a partially cutaway side elevation schematic view of the contact lens cleaning device 10, illustrating normal operation with the main housing portion 30 inverted over and attached to the solution-filled base portion 20. This view illustrates the connecting rods 70a, b, and therefore the lens holder 40, at maximum (downward) extension. Guide bar 74 is shown riding in guide bar slot 76 for stabilization of the reciprocating travel. This view further illustrates the effect of connecting rods 70a, b, and their respective hinges 78a, b to act as "dams" to fluid flow. As the lens holder is raised through the solution, the fluid is unable to flow around the ends of the lens holder due to the barrier formed by these structures. Instead, the solution is forced downward through the lens baskets, thereby enhancing the cleaning of the lenses. In addition, guide bar 74 acts in a similar manner as a barrier to solution flow between the two sides of the lens holder. The offset nature of cross straps 43 and 49 is also visible in this view, which feature further enhances the efficient cleaning of the contact lenses.

Figure 7:
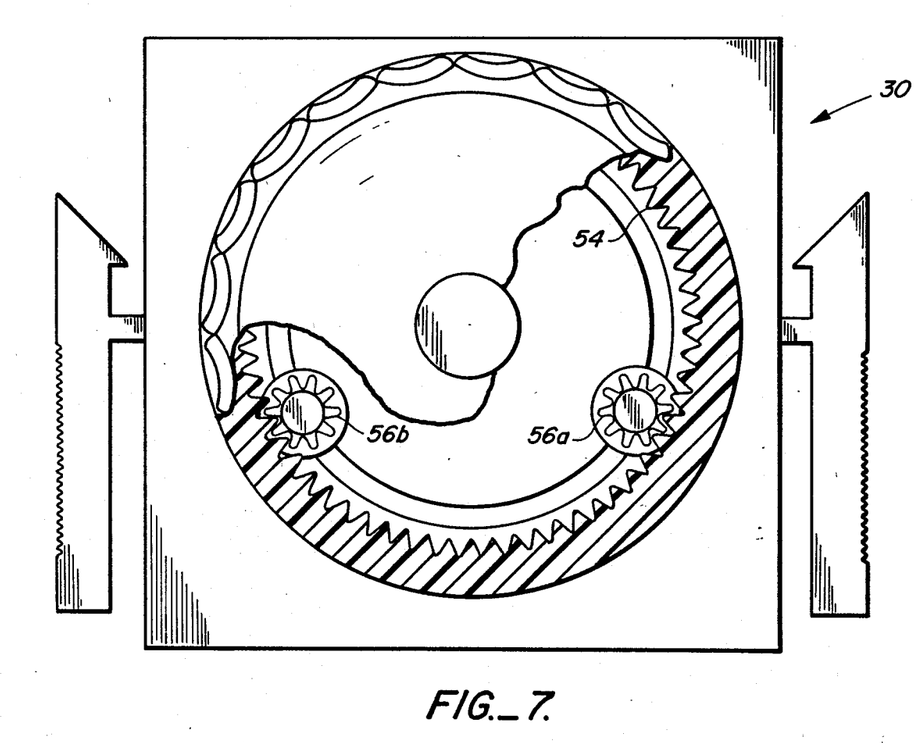
FIG. 7 is a partially cutaway rear elevation view of the main housing portion of the contact lens cleaning device, illustrating the engagement of the internal ring gear and crankshaft pinion gears.

FIG. 7 is a partially cutaway rear elevation view of the main housing portion 30 of the contact lens cleaning device, illustrating the engagement of the internal ring gear 54 and crankshaft pinion gears 56a, b. In this arrangement, both pinion gears are driven in the same direction. Inclusion of an idler gear between one of the pinions would effectively result in counter rotating crankshafts, which may be desirable for some applications. Of course, any number of teeth could be used for these respective gears, but it has been found that sixty teeth on the internal ring gear to ten teeth in the pinion gears provides a suitable gearing for lens holder reciprocations/cleaning.

Figure 8:
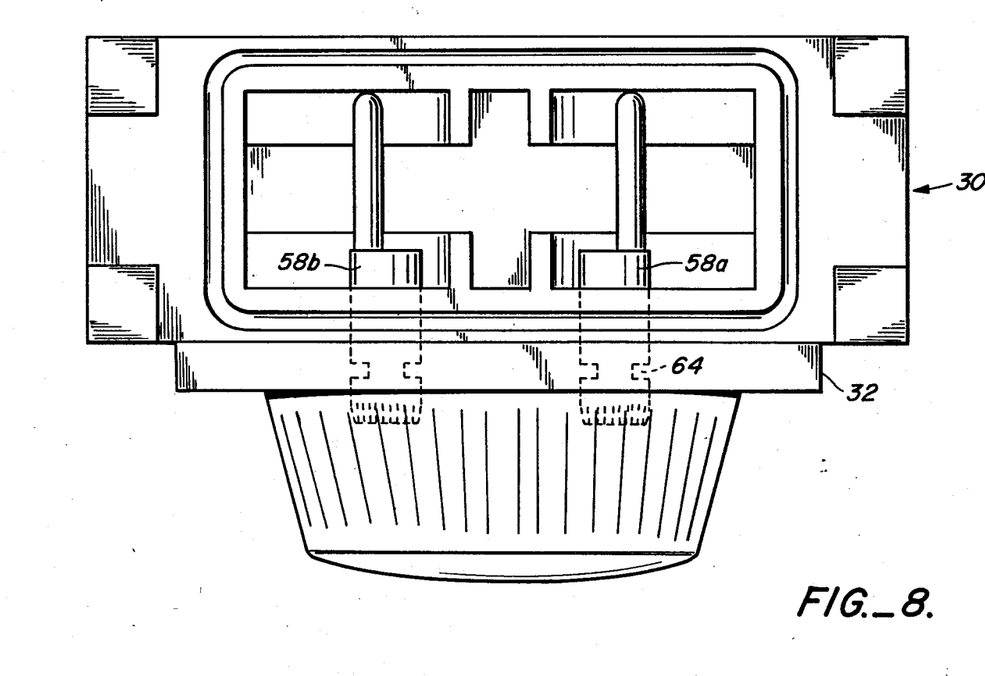
FIG. 8 is a top plan view of the main housing portion of the contact lens cleaning device with the installed crankshafts shown in phantom.

FIG. 8 is a top plan view of the main housing portion 30 of the contact lens cleaning device, with the installed crankshafts 58a, b shown in phantom. This view also illustrates the sealing capability of 0-rings 64 within main body 32.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:
1. A contact lens cleaning device comprising:
a housing member bearing an internal cavity for containing a cleaning solution;
a lens holder portion for releasable capture of said contact lens, said lens holder portion terminating in end portions separated by a first distance, said lens holder portion conditioned for reciprocating motion within said housing member;
connecting rod means attached to said lens holder portion, said connecting rod means comprising a pair of connecting rods each attached to only one of said lens holder end portions; and
rotary drive means connected to said connecting rod means, said rotary drive means comprising a pair of crankshafts each bearing an off-center crankpin, said crankpins attached to said connecting rods so that said crankpins are separated by a second distance lens than said first distance, so that rotation of said rotary drive means moves said lens holder portion in reciprocating motion.

2. The contact lens cleaning device of claim 1 wherein said crankshafts are each driven by a common gear, and said common gear is connected to said housing member.

3. The contact lens cleaning device of claim 1 wherein said lens holder portion includes a pair of lens baskets each having an outer basket and an inner lens support, each comprising a plurality of radially-extending cross straps, said outer basket cross straps radially offset to said lens support cross straps.

4. The contact lens cleaning device of claim 1 wherein said connecting rods are attached to said lens holder portion in a manner to create a barrier to fluid flow.

* * * * *